US009588105B1

(12) United States Patent
Hussain et al.

(10) Patent No.: US 9,588,105 B1
(45) Date of Patent: Mar. 7, 2017

(54) PORTABLE IN VITRO MULTI-WELL CHAMBER FOR EXPOSING AIRBORNE NANOMATERIALS AT THE AIR-LIQUID INTERFACE USING ELECTROSTATIC DEPOSITION

(71) Applicant: The United States of America, as represented by the Secretary of the Air Force, Washington, DC (US)

(72) Inventors: Saber M. Hussain, Beavercreek, OH (US); Christin M. Grabinski, Centerville, OH (US); James E. Grabinski, Lowell, IN (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 274 days.

(21) Appl. No.: 14/214,168

(22) Filed: Mar. 14, 2014

Related U.S. Application Data

(60) Provisional application No. 61/786,747, filed on Mar. 15, 2013.

(51) Int. Cl.
*G01N 33/00* (2006.01)
*G01N 33/50* (2006.01)
(Continued)

(52) U.S. Cl.
CPC ......... *G01N 33/5008* (2013.01); *C12M 23/12* (2013.01); *C12M 25/00* (2013.01);
(Continued)

(58) Field of Classification Search
CPC .......................... C12M 35/02; G01N 33/5008
See application file for complete search history.

(56) References Cited

U.S. PATENT DOCUMENTS 5,247,842 A * 9/1993 Kaufman ................ B05B 5/002
356/37
5,308,758 A * 5/1994 Dahl ...................... C12M 41/46
435/287.1

(Continued)

FOREIGN PATENT DOCUMENTS

WO    WO 2012/164008    12/2012

OTHER PUBLICATIONS

Savi, M., et al., "A novel exposure system for the efficient and controlled deposition of aerosol particles onto cell cultures," Environ. Sci. Technol. 2008; 42: 5667-5674.
(Continued)

*Primary Examiner* — Jonathan Hurst
(74) *Attorney, Agent, or Firm* — AFMCLO/JAZ; Timothy Barlow

(57) ABSTRACT

A single- or multi-well chamber assembly comprising nanoparticle exposure chambers with a plurality of wells designed to hold porous membrane inserts, with cell culture media being maintained on the basal (lower) surface to generate the air-liquid interface. The wells may accommodate a variety of sizes of cell culture inserts and may be arranged radially. The chamber assembly comprises an integrated heating-humidifying mechanism so that the internal chamber environment may be heated to 37° C. and maintained at humid conditions to allow for maintenance of cell cultures. The presently disclosed apparatus may be used to investigate the toxicity of airborne nanoparticles to cells or tissue models grown at the air-liquid interface. Aerosolized nanomaterials are drawn into a multi-well chamber assembly and deposited via electrostatic deposition onto cells grown at the air-liquid interface.

11 Claims, 8 Drawing Sheets

(51) Int. Cl.
C12M 1/00 (2006.01)
C12M 1/12 (2006.01)
C12M 1/36 (2006.01)
C12M 1/32 (2006.01)
C12M 1/42 (2006.01)
(52) U.S. Cl.
CPC ............ C12M 29/00 (2013.01); C12M 35/02 (2013.01); C12M 41/48 (2013.01); C12M 47/00 (2013.01)

(56) References Cited

U.S. PATENT DOCUMENTS

| | | | |
|---|---|---|---|
| 6,060,128 | A | 5/2000 | Kim |
| 6,093,557 | A * | 7/2000 | Pui .................. C12N 15/895 435/173.1 |
| 7,926,368 | B2 | 4/2011 | Ryan |
| 7,972,841 | B2 | 7/2011 | Massey et al. |
| 8,178,341 | B2 | 5/2012 | Petrucci |
| 8,225,681 | B2 | 7/2012 | Paur et al. |
| 8,426,157 | B2 | 4/2013 | Knebel |
| 2002/0132286 | A1 | 9/2002 | Downs |
| 2005/0170499 | A1 | 8/2005 | Mohr et al. |
| 2006/0099706 | A1 | 5/2006 | Massey et al. |
| 2006/0127966 | A1 | 6/2006 | Ryan |
| 2006/0128008 | A1 | 6/2006 | Ryan |
| 2007/0164216 | A1* | 7/2007 | Fedorov .............. B82Y 35/00 250/309 |
| 2008/0047825 | A1* | 2/2008 | Petrucci ............... B82Y 5/00 204/164 |
| 2010/0009335 | A1* | 1/2010 | Joseph ............... C12M 23/12 435/3 |
| 2010/0273246 | A1 | 10/2010 | Fukano et al. |
| 2011/0212515 | A1* | 9/2011 | Mohr .................. C12M 23/00 435/289.1 |

OTHER PUBLICATIONS

Kim, J.S., et al., "Validation of an in vitro exposure system for toxicity assessment of air-delivered nanomaterials," Toxicology in Vitro (2013) 27: 164-173.
Xie, Y., et al., "Aerosolized ZnO nanoparticles induce toxicity in alveolar type II epithelial cells at the air-liquid interface," Toxicological Sciences 2012; 125: 450-461.
Mülhopt, S., et al., "Lung toxicity determination by in vitro exposure at the air liquid interface with an integrated online dose measurement," Journal of Physics: Conference Series 2009; 170: 012008, 5 pages.
Diabeté, S., et al., "Biological effects in human lung cells exposed to platinum nanoparticle aerosol," European Aerosol Conference 2009, Karlsruhe, Abstract T013A02.
Diabeté, S., et al., "The response of a co-culture lung model to fine and ultrafine particles of incinerator fly ash at the air-liquid interface," ATLA 2008; 36: 285-298.
Aufderheide, M., "Analytical in vitro approach for studying cyto- and genotoxic effects of particulate airborne material," Analytical Bioanalysis Chemistry 2011; 401: 3213-3220.
Pohl, C., et al., "Prevalidation of the Cultex method: In vitro analysis of the acute toxicity of inhalable fine dusts and nanoparticles after direct exposure of cultivated human cells from the respiratory tract," Toxicology Letters 2011; 205S: S171-S172, Poster abstract, EUROTOX.
Paur, H.R., et al., "In vitro exposure systems and bioassays for the assessment of toxicity to nanoparticles to the human lung," Journal of Consumer Protection and Food Safety. 2008; 3: 319-329.
Knebel, J.W., et al., "Exposure of human lung cells to native diesel motor exhaust—Development of an optimized in vitro test strategy," Toxicology in Vitro 2002; 16: 185-192.
Tippe, A., et al., "Deposition of fine and ultrafine aerosol particles during exposure at the air/cell interface," Journal of Aerosol Science, 2002; 33: 207-218.

Bitterle, E., et al., "Dose-controlled exposure of A549 epithelial cells at the air-liqud interface to airborne ultrafine carbonaceous particles," Chemosphere 2006; 65:1784-1790.
Brandenberger, C., et al., "Effects and uptake of gold nanoparticles deposited at the air-liquid interface of a human epithelial airway model," Toxicology and Applied Pharmacology 2010; 242: 56-65.
Lenz, A.G., et al., "A dose-controlled system for air-liquid interface cell exposure and application to zinc oxide nanoparticles," Particle and Fibre Toxicology 2009; 6: 32.
Grigg, J., et al., "DNA damage of macrophages at an air-tissue interface induced by metal nanoparticles," Nanotoxicology, 2009; 3(4): 348-354.
Stokes, W.S., et al., "Recent progress and future directions at NICEATM-ICCVAM: Validation and regulatory acceptance of alternative test methods that reduce, refine, and replace animal use," Altex 27 (2010) Special Issue 221-232.
Saffari, H., et al., "Electrostatic deposition of nanoparticles into live cell culture using an electrospray differential mobility analyzer (ES-DMA)," Journal of Aerosol Science 2012; 48: 56-62.
Hoet, Peter HM, et al., "Nanoparticles-known and unknown health risks," Journal of Nanobiotechnology, 2004, 2:12, 15 pages.
Geiser, M., et al., "Deposition and biokinetics of inhaled nanoparticles," Particle and Fibre Toxicology 2010, 7:2, 17 pages.
Nel, A., et al., "Toxic Potential of Materials at the Nanolevel," Science 311 (2006) 622-627.
Yu, K.O., et al., "Toxicity of amorphous silica nanoparticles in mouse keratinocytes," J Nanopart Res (2009) 11:15-24.
Kearns, C.R., "In Vitro Toxicity of Silver Nanoparticles in Human Lung Epithelial Cells," Thesis Presented to Air Force Institute of Technology in Partial Fulfillment of the Requirements for the Degree of Master of Science, Mar. 2009, 99 pages.
Hussain, S.M., et al., "Biological Interactions of Nanomaterials," Final Report AFRL-RH-WP-TR-2009-0044, Dec. 2008, 124 pages.
Grabinski, C., et al., "Effect of Gold Nanorod Surface Chemistry on Cellular Interactions In Vitro," ACS Nano 2011; 5: 2870-2879.
Kim, J.S., Evaluating pulmonary toxicity of engineered metal-based nanoparticles using in vivo and in vitro models, Thesis submitted in partial fulfillment of the requirements for the Doctor of Philosophy degree, Dec. 2011, 141 pages.
Geiser, M., et al., "Cellular responses after exposure of lung cell cultures to secondary organic aerosols," Abstract, AAAR 2010 International Specialty Conference, Mar. 22-26, 2010, San Diego, CA.
Holder, A.L., et al., "Cellular Response to Diesel Exhaust Particles Strongly Depends on the Exposure Method," Toxicological Sciences 103(1), 108-115 (2008).
Volckens, J., et al., "Direct particle-to-cell deposition of coarse ambient particulate matter increases the production of inflammatory mediators from cultured human airway epithelial cells," Environ Sci Technol. Jun. 15, 2009; 43(12): 4595-4599.
Hebestreit, M., et al., "Dose Determination of Airborne Particles for In Vitro Exposure at the Air / Liquid Interface," Poster abstract, IVTIP Spring Meeting 2012, Apr. 19, 2012 Bilbao, Spain.
Geys, J., et al., "Assay conditions can influence the outcome of cytotoxicity tests of nanomaterials: Better assay characterization is needed to compare studies," Toxicology in Vitro 2010; 24: 620-629.
Grabinski, C., et al., "Effect of particle dimension on biocompatibility of carbon nanomaterials," Carbon 2007; 45: 2828-2835.
Gupta, A., et al., "Generation of C60 nanoparticle aerosol in high mass concentrations," Journal of Aerosol Science 2007; 38: 592-603.
Hussain, S.M., et al., "Toxicity evaluation for safe use of nanomaterials: Recent achievements and technical challenges," Advanced Materials 2009; 21: 1549-1559.
Park, M.V.D.Z., et al., "The status of in vitro toxicity studies in the risk assessment of nanomaterials," Nanomedicine 2009; 4: 669-685.
Schaeublin, N.M., et al., "Surface charge of gold nanoparticles mediates mechanism of toxicity," Nanoscale 2011; 3:410-420.
Hussain, S.M., et al., "Toxicological Highlight—Safety Evaluation of Silver Nanoparticles: Inhalation Model for Chronic Exposure," Toxicological Sciences 108(2), 223-224 (2009).

(56) References Cited

OTHER PUBLICATIONS

Husssain, S.M., et al., "In Vitro Toxicity of Nanoparticles in BRL 3A Rat Liver Cell Lines," Final Report for the Period May 2003-May 2004, AFRL-HE-WP-TR-2004-0048 (May 2004).

Zhu, L., et al., "Assessment of Human Lung Macrophages After Exposure to Multi-Walled Carbon Nanotubes Part I. Cytotoxicity," Nanoscience and Nanotechnology Letters vol. 3, 88-93, 2011.

Zhu, L., et al., "Assessment of Human Lung Macrophages After Exposure to Multi-Walled Carbon Nanotubes Part II. DNA Damage," Nanoscience and Nanotechnology Letters vol. 3, 94-98, 2011.

Wiedensohler, A., "Technical Note—An Approximation of the Bipolar Charge Distribution for Particles in the Submicron Size Range," J. Aerosol Sci., vol. 19, No. 3, pp. 387-389, 1988.

British American Tobacco, "Whole Smoke Exposure System," Published 2009, XP55029541, available at <http://www.bat-science.com/groupms/sites/bat_7awfh3.nsf/vwPagesWebLive/DO7AXGRG/$FILE/medMD7RXCVE.pdf?openelement >.

\* cited by examiner

PORTABLE IN VITRO MULTI-WELL CHAMBER FOR EXPOSING AIRBORNE NANOMATERIALS AT THE AIR-LIQUID INTERFACE USING ELECTROSTATIC DEPOSITION

CROSS-REFERENCE TO RELATED APPLICATIONS

This application claims the benefit of U.S. Provisional Application No. 61/786,747, filed Mar. 15, 2013, which is herein incorporated by reference in its entirety.

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

This invention relates generally to the field of particle deposition on a material. More particularly, it relates to an apparatus for the deposition of nanoparticles onto a biological material.

2. Description of the Related Art

Nanomaterials (NMs) are generally defined as a material with a base constituent that is between $1\times10^{-9}$ and $100\times10^{-9}$ meters in length with at least one property that deviates from the equivalent bulk material. Nanotechnology is driven largely by the idea that the ability to manipulate NMs by advanced synthesis methods and surface modifications will lead to tailorable and enhanced properties. Continuous innovation in synthesis and characterization of NMs have led to a more advanced understanding of the relationship between nanostructure and properties, and the exploitation of properties inherent to materials at the nano-scale has resulted in rapid growth in the field of nanotechnology. For example, aluminum NMs have been used by the U.S. Army in solid rocket fuel and by the U.S. Naval Air Warfare Center to replace lead primers in artillery and wear-resistant coatings on propeller shafts.

Changes in physicochemical properties at the nano-scale are the basis of the unique nature and value of NMs. However, these properties are also cause for concern regarding the toxicological effects of NMs on biological systems. When inhaled, NMs are capable of depositing deep within the alveolar portion of the respiratory tract and may induce local inflammation and oxidative stress. NMs may also be introduced into the body via dermal contact and ingestion, and the ability of NMs to pass through cell membranes and tissues or be distributed throughout the lymphatic and circulatory systems could result in unintended hazardous consequences. Because NMs are smaller than eukaryotic cells and most organelles, they may be taken up within these structures, potentially interfering with cellular processes. In addition to size, additional properties of NMs that can cause interaction with cells include surface chemistry, surface charge, stability (e.g. ion dissolution), and purity. Chronic exposure to NMs in air pollution has been linked to a variety of diseases, including cardiovascular disease, asthma, and diabetes.

While there are advantages and drawbacks for both in vitro and in vivo NM toxicity studies, there is strong motivation to improve alternative techniques to reduce, replace, or refine the use of animals. Due to the costs and ethical issues associated with in vivo toxicity studies, it is critical to improve in vitro techniques for more rapid testing of toxicity of NMs, which include a diverse and rapidly expanding range of materials. Traditional in vitro assays require that NMs be dispersed in biological media and administered to cells, which can induce NM aggregation. These techniques may also alter the properties of NMs and do not mimic realistic inhalation exposure, often yielding contradictory and inconclusive results. Additionally, the dosimetry is very difficult to predict in NM dispersion, which is the often the most critical feature of toxicity investigations. When NMs are exposed to the lung via inhalation, they are deposited in the gas phase onto cell layers covered in a thin layer of mucus, making in vitro studies at the air-liquid interface an appropriate mechanism for investigating the inhalation toxicity of NMs.

Major challenges associated with building a system for exposing at the air-liquid interface include controlled particle generation, predictable and uniform particle deposition, and controlled cellular environment (100% humidity, 37° C.). A complete system must generally include strategically placed conductive components for electrostatic deposition of NMs, adjustable inlet tube heights, in addition to well-designed heating and humidity generation/monitoring. Previous attempts to study NM toxicity at the air-liquid interface have run into a number of problems, including particle agglomeration and uneven particle distribution and dosing.

SUMMARY OF THE INVENTION

The present invention includes a nanoparticle exposure system comprising: a gas supply that provides a gas flow comprising, for example, 5% $CO_2$ and 95% filtered dry air or $N_2$; an aerosol nanoparticle generator coupled to and in fluid communication with the gas supply, in which the aerosol nanoparticle generator generates a plurality of charged nanoparticles using an electrospraying process, the charged nanoparticles mixing with the gas flow from the gas supply to form a charged nanoparticle flow; an ionizing source coupled to and in fluid communication with the aerosol particle generator; a nanoparticle exposure chamber assembly coupled to and in fluid communication with ionizing source, with the nanoparticle exposure chamber assembly comprising at least one nanoparticle exposure chamber; a high voltage source coupled to the nanoparticle exposure chamber assembly; an exterior pump coupled to the nanoparticle exposure chamber assembly such that a high voltage is applied to the at least one nanoparticle exposure chamber; and a control system coupled to at least one component of the nanoparticle exposure system such that the control system regulates the operation of and logs data from the nanoparticle exposure system.

In one embodiment, the ionizing source partially neutralizes the charged nanoparticles such that the charged nanoparticles remain evenly distributed as an aerosol.

In another embodiment of the nanoparticle exposure system, the nanoparticle exposure chamber assembly comprises: an aerosol inlet that is coupled to and in fluid communication with the ionizing source such that the charged nanoparticle flow enters the nanoparticle exposure chamber assembly, at least one inlet passageway that is coupled to and in fluid communication with the aerosol inlet and terminates in a conical inlet tube, with each conical inlet tube further comprising a wire mesh across a diameter of the conical inlet tube, each conical inlet tube being coupled to and in fluid communication with one of the at least one nanoparticle exposure chambers; a discharge port coupled to and in fluid communication with at least one of the nanoparticle exposure chambers, in which each discharge port is configured concentrically about an outside diameter of one conical inlet tube, with the discharge port further being coupled to and in fluid communication with at least one outlet passageway, in which each outlet passageway is coupled to and in fluid communication with an aerosol outlet that is further coupled to in fluid communication with the exterior pump; and an integrated heater and humidifier comprising a heat source and a humidity source, with the integrated heater and humidifier being coupled to and in fluid communication with at least one inlet passageway.

In an additional embodiment, each nanoparticle exposure chamber comprises: a cell culture well configured to receive a cell culture insert located directly beneath the conical inlet tube, in which the cell culture insert is configured to hold a target; a media well comprising cell culture media, in which the media well is located beneath the cell culture well such that at least a portion of the target is in contact with the cell culture media to create an air-liquid interface and such that the integrated heater and humidifier is in contact with the media well; and a grounded electrode located beneath the media well.

In a further embodiment, the integrated heater and humidifier further comprises a wicking material that facilitates entry of humidity from the humidity source into the inlet passageway.

In another embodiment, the high voltage source is coupled to the nanoparticle exposure chamber assembly such that an electric field is applied across the target, with an electric field strength being dependent on a distance between the wire mesh and the grounded electrode, in which the nanoparticle exposure system is configured to deliver a dose of charged nanoparticles over a predetermined period of time. In one embodiment, the nanoparticle exposure chamber assembly is configured such that the distance between the wire mesh and the grounded electrode for each nanoparticle exposure chamber is adjustable by a common adjustment mechanism, with the distance being the same for all chambers.

In a further embodiment comprising two or more nanoparticle exposure chambers, the chambers are arranged radially about a central axis of the nanoparticle exposure chamber assembly. In yet another embodiment, at least a portion of each nanoparticle exposure chamber further comprises a resealable sleeve. In one embodiment, the nanoparticle exposure chamber assembly further comprises a channel between the sleeve and an exterior of the nanoparticle exposure chamber assembly, with the resealable sleeve permitting the cell culture media to be replenished or replaced without compromising the sterility of the nanoparticle exposure chamber assembly.

In another embodiment, the exterior pump draws the charged nanoparticle flow into the nanoparticle exposure chamber assembly. In a further embodiment, the nanoparticle exposure chamber assembly further comprises a plurality of modular stacking plates arranged about a central axis of the nanoparticle exposure chamber assembly, in which the modular stacking plates are interconnected and configured to be independently adjusted. Each modular stacking plate comprises a portion of the nanoparticle exposure chamber assembly. In an additional embodiment, the nanoparticle exposure system further comprises at least one particle characterization device.

The present invention further includes a nanoparticle exposure chamber assembly in which the integrated heater and humidifier is in contact with the media well such that the cell culture media is maintained at or near 37° C., with the integrated heater and humidifier being coupled to and in fluid communication with at least one inlet passageway.

The present invention further includes a nanoparticle exposure chamber assembly comprising: a plurality of nanoparticle exposure chambers radially arranged about a central axis of the nanoparticle exposure chamber assembly, in which at least a portion of each nanoparticle exposure chamber comprises a resealable sleeve and a channel between the resealable sleeve and an exterior of the nanoparticle exposure chamber assembly, with the resealable sleeve permitting the cell culture media to be replenished or replaced without compromising the sterility of the nanoparticle exposure chamber assembly. The nanoparticle exposure chamber assembly further comprises a plurality of modular stacking plates arranged about a central axis of the nanoparticle exposure chamber assembly, with the modular stacking plates being interconnected and being configured to be independently adjusted. Each modular plate comprises a portion of the nanoparticle exposure chamber assembly.

DETAILED DESCRIPTION OF THE INVENTION

Figure 1A:
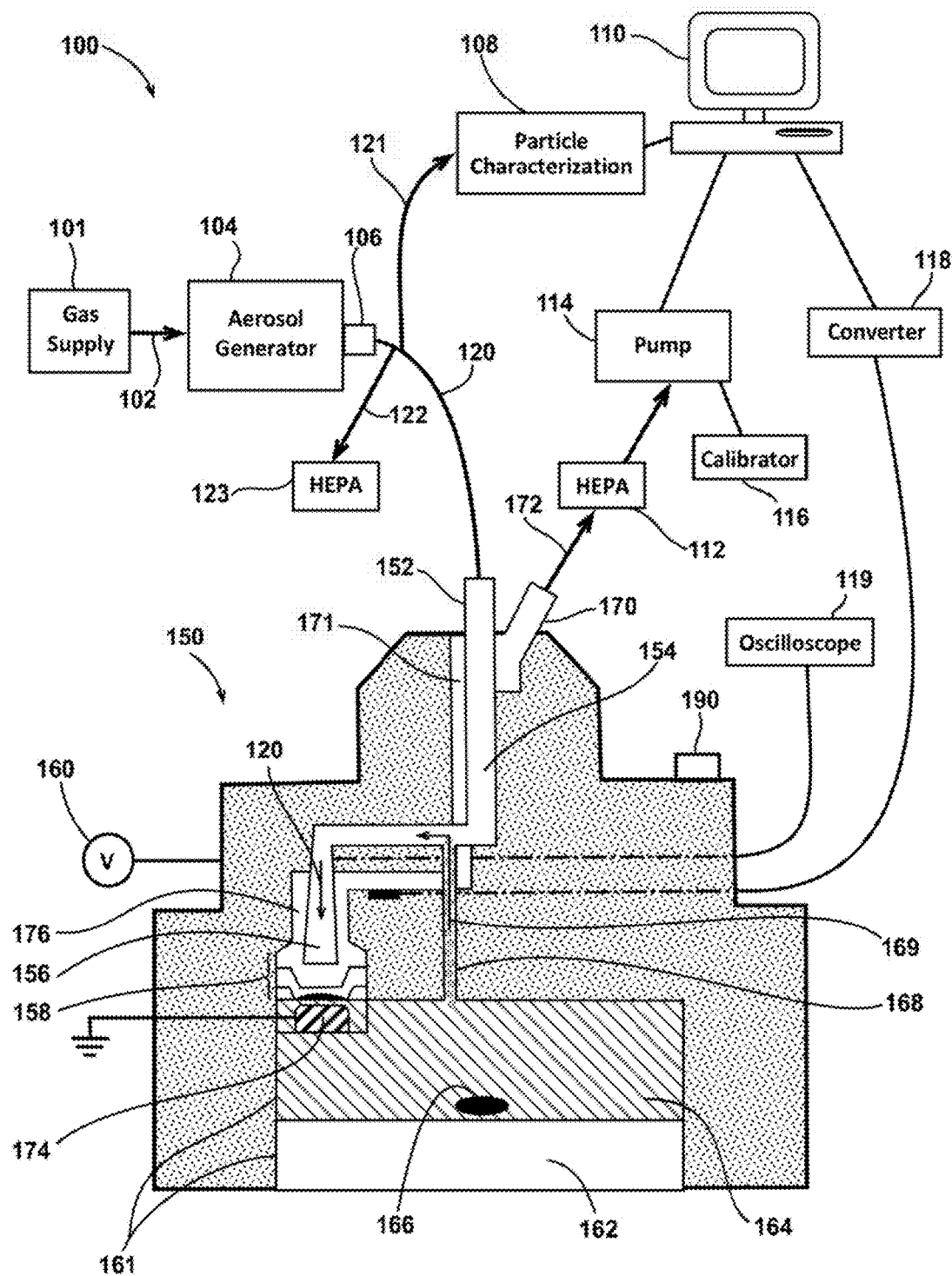
FIG. 1A is a high-level view of one embodiment of a nanoparticle exposure system comprising a nanoparticle exposure chamber assembly, which is shown enlarged and in cross-section.

The presently disclosed apparatus includes a single- or multi-well nanoparticle exposure chamber assembly comprising one or more nanoparticle exposure chambers each comprising one well designed to hold a porous membrane insert, with cell culture media being maintained on the basal (lower) surface to generate the air-liquid interface. The wells may accommodate a variety of sizes of cell culture inserts and may be arranged, for example, radially about a central axis. The internal chamber environment may be held at a desired humidity and temperature using a water bath and a heating or cooling mechanism, both of which are fully integrated into and contained within the assembly. The heating mechanism may comprise a heater-stirrer plate, which stirs a water bath inside the base of the chamber to maintain even heating throughout the internal chamber. The water bath further provides humidity that is distributed throughout the chamber assembly. The temperature and humidity may be monitored using sensors mounted near the cell layer, and temperature and humidity data may be collected and stored using a data logger. The presently disclosed apparatus may be used to investigate the toxicity of airborne nanoparticles to cells or tissue models grown at the air-liquid interface. For example, aerosolized NMs are drawn into the chamber assembly and deposited via electrostatic deposition onto cells grown at the air-liquid interface.

The presently disclosed apparatus offers a number of advantages, including fully integrated heating and humidity components and internal humidity and temperature monitoring capabilities so that the cell cultures may remain in the apparatus throughout the entirety of the experiment. For example, the assembly may maintain 100% humidity and a 37° C. temperature to better replicate in vivo conditions. In addition, the apparatus may comprise multiple chambers in a radial arrangement, with the wells being configured to accept different sizes of cell culture inserts. Access to the cells and to the cell culture media may be controlled through resealable sleeves and may use an introducer sheath, both of which allow the cell culture media to be replenished during the experiment while still maintaining sterility.

Many currently available exposure chambers and devices require that the cell cultures be removed after exposure, which may increase cell trauma and death and may distort the experimental results. In addition, all operations involving the cell cultures must be done in a biohood to maintain sterility in many conventional nanoparticle exposure chambers. The use of resealable sleeves in the presently disclosed nanoparticle exposure system allows many of these operations to be performed in any environment. Cell culture media may be replenished or replaced at any time, which may be particularly useful for toxicity assays immediately following nanoparticle exposure such as monitoring of lactate dehydrogenase leakage.

In addition, any currently available exposure chambers do not provide sufficient mechanisms to deposit a small, controlled amount of NMs over a long period of time. The presently disclosed apparatus allows the distance between the inlet tube and the cell layer and/or electrode to be adjusted and comprises an integrated electrostatic deposition device, both of which allow for controlled NM dosage. Because the presently disclosed nanoparticle exposure chamber assembly is almost entirely self-contained, it allows for exposing cell and tissue cultures to lower, precisely controlled, biologically relevant doses of NMs over a longer period of time, the results of which better replicate in vivo experiments.

Referring to the drawings, like reference numerals may designate like or corresponding parts throughout the several views. Portions of the nanoparticle exposure system and/or chamber assembly and labeling of some components have been omitted in some views for clarity and to illustrate certain aspects of the invention in detail. These variations should in no way be interpreted as limiting the scope of the invention.

FIG. 1A is a high-level view of one embodiment of a nanoparticle exposure system 100 comprising a nanoparticle exposure chamber assembly 150, which is shown enlarged and in cross-section. A gas supply 101 supplies a gas flow 102, which enters an aerosol particle generator 104. The gas flow 102 may comprise, for example, carbon dioxide ($CO_2$; 5%) plus air (95%) or nitrogen ($N_2$; 95%). The aerosol particle generator 104 may generate NM aerosols using an electrospraying process. An example of a suitable electrospray device includes an Electrospray Aerosol Generator Model 3480 (TSI®), which has been demonstrated to produce monodisperse NM aerosols. The electrospray device operates by drawing a conductive buffer containing dispersed NMs into a capillary by applying a pressure drop. An electric field is applied, drawing the liquid into a conical jet, which breaks up into ultrafine charged droplets. For dilute liquid dispersions, each droplet contains ≤1 nanoparticle, allowing for uniform aerosolization. Once droplets containing nanoparticles are formed, the liquid evaporates, leaving highly charged nanoparticles in the gas phase. The nanoparticles may generally be between $1 \times 10^{-9}$ and $100 \times 10^{-9}$ meters in size. In some embodiments, the charge on the nanoparticles may be partially neutralized by a sealed ionizing source 106 comprising an ionizer such as polonium 210 to prevent agglomeration. The charged nanoparticles are then mixed with a flow of filtered dry air (95%) and carbon dioxide ($CO_2$; 5%) from the gas supply to create a charged nanoparticle flow 120. The 95% filtered dry air may optionally be replaced with 95% nitrogen ($N_2$) to prevent oxidation of nanoparticle exposure system 100 components and/or to create hypoxic conditions in the nanoparticle exposure chamber assembly 150.

The charged nanoparticle flow 120 leaving the sealed ionizing source 106 may have a flow rate of approximately one liter/minute. A first portion 121 of the charged nanoparticle flow 120 is diverted to a particle characterization device 108, which may comprise one or more devices that provide information about the nanoparticles including number and size. An example of a suitable particle counter includes a Condensation Particle Counter Model 3007 (TSI®), which operates by condensing alcohol on the surface of aerosols so that they are large enough to be optically detected. The particle detection size range is generally 10 nm to >1 µm. An example of a suitable particle sizer includes a scanning mobility particle sizer NanoScan Model 3910 (TSI®), which operates by passing the charged aerosols through a radial differential mobility analyzer to separate particles by size as they are passed into a particle counter to allow for characterization of the size distribution of the NM aerosols. The first portion 121 of the charged nanoparticle flow 120 may comprise approximately 0.7 liters/minutes. A second portion 122 of the charged nanoparticle flow 120 may be diverted to a HEPA filter 123 in order to achieve the desired rate of nanoparticle flow 120 into the nanoparticle exposure chamber assembly 150. The second portion 122 may be approximately 0.22 liters/minute and/or the remaining/excess portion of the charged nanoparticle flow 120 that does not enter the particle characterization device 108 or the nanoparticle exposure chamber assembly 150.

The nanoparticle exposure system 100 further comprises a control system 110, which may comprise a microprocessor and a variety of other components including one or more controllers and a data logger (not separately labeled) and may comprise a computer or computer system. In the embodiment shown in FIG. 1A, the control system 110 is depicted as being coupled to various components, including the particle characterization device 108, the pump 114, and/or the converter 118 for the sensor data. A person of ordinary skill will appreciate that the control system 110 may comprise additional components and may be coupled or operatively connected to additional components of the nanoparticle exposure system 100 in order to make the nanoparticle exposure system 100 operable.

Figure 5:
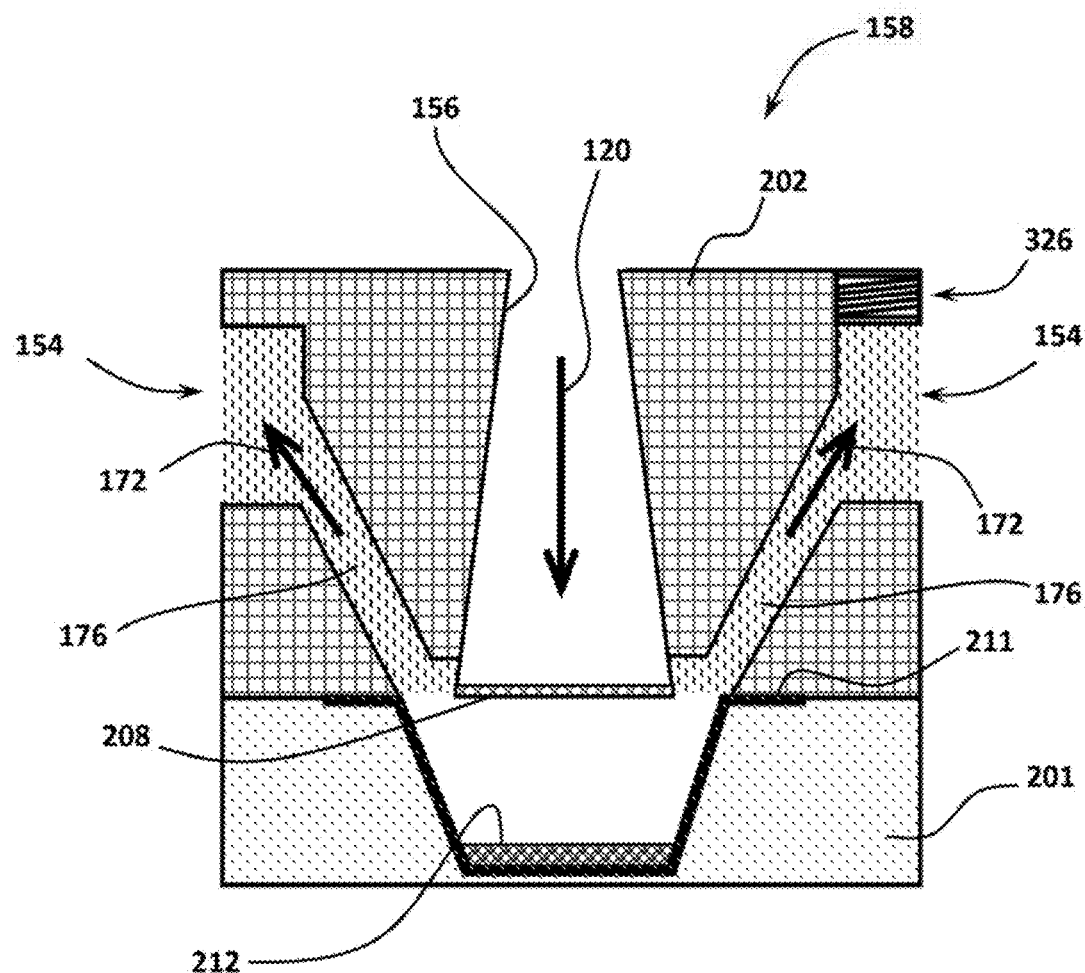
FIG. 5 is a cross-sectional view of a further embodiment of the nanoparticle exposure chamber.

The charged nanoparticle flow 120 enters the nanoparticle exposure chamber assembly 150 via an aerosol inlet 152 at a much reduced flow rate, for example approximately 0.08 liters/minute. The aerosol inlet 152 leads to a series of internal inlet passageways 154 that each terminate in a conical inlet tube 156 in which the internal diameter gradually increases until the conical inlet tube 156 terminates at the top of a nanoparticle exposure chamber 158. For clarity, a single internal inlet passageway 154 leading to one nanoparticle exposure chamber 158 is depicted in FIG. 1A. In other embodiments, the aerosol inlet 152 may be coupled to two or more internal inlet passageways 154 that are coupled to and feed into a corresponding number of nanoparticle exposure chambers 158. Each nanoparticle exposure chamber 158 is coupled to a single internal inlet passageway 154, and individual nanoparticle exposure chambers 158 may be independently isolated or closed off from the charged nanoparticle flow 120. The charged nanoparticle flow 120 exits the conical inlet tube 156 to enter the nanoparticle exposure chamber 158. Only a portion of the components of the nanoparticle exposure chamber 158 are shown and/or labeled in FIG. 1A. A detailed view of a nanoparticle exposure chamber 158 is depicted in FIGS. 2-3 and 5.

In some embodiments, the nanoparticle exposure chamber assembly 150 comprises a plurality of nanoparticle exposure chambers 158 arranged radially about a central axis of the nanoparticle exposure chamber assembly 150. In one embodiment, the nanoparticle exposure chamber assembly 150 comprises eight radially arranged nanoparticle exposure chambers 158 (see FIG. 4 for more detail). This radial arrangement of the nanoparticle exposure chambers 158 is desirable as it allows a more even distribution of the charged nanoparticle flow 120 to all of the nanoparticle exposure chambers 158. In addition, having multiple nanoparticle exposure chambers 158 allows the user to run experiments in duplicate or triplicate with controls.

A wire mesh (not labeled; see FIGS. 2-3 and 5 for additional detail) is embedded across an entire diameter of the discharge end of the conical inlet tube 156, and a grounded electrode 174 is positioned at the bottom of the nanoparticle exposure chamber 158. A function generator (not separately labeled) is used to convert electricity into a waveform of interest. An example of a suitable function generator includes the BK Precision® 4010A function generator. The function generator may further comprise a power amplifier such as the Trek® Model 609B high voltage power amplifier. High voltage 160 is applied to the conical inlet tube 156, and the electric field generated between the wire mesh and the grounded electrode 174 is a function of the voltage applied and the distance between the two components.

Figure 2:
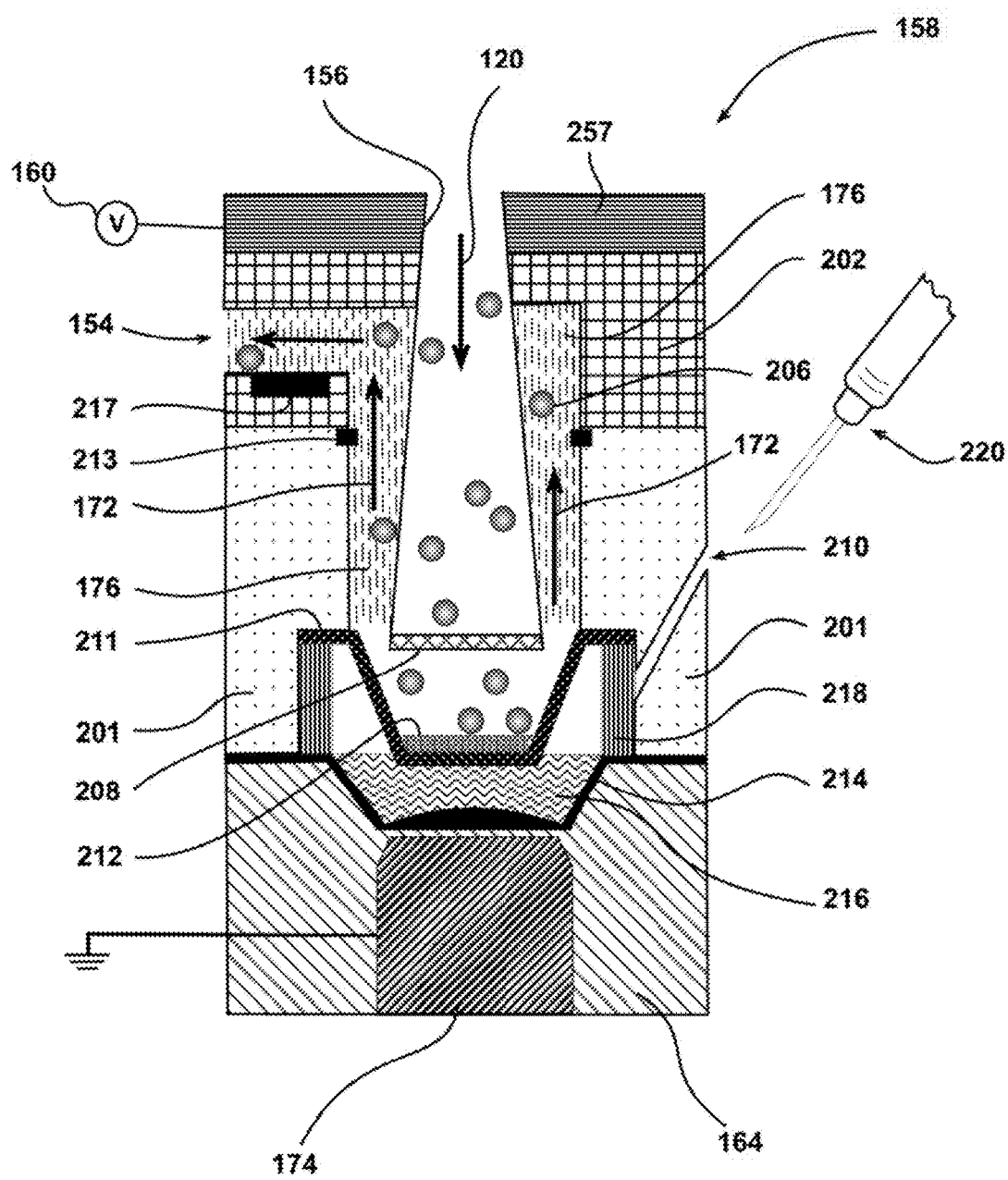
FIG. 2 is a cross-sectional view one embodiment of a nanoparticle exposure chamber.
Figure 3:
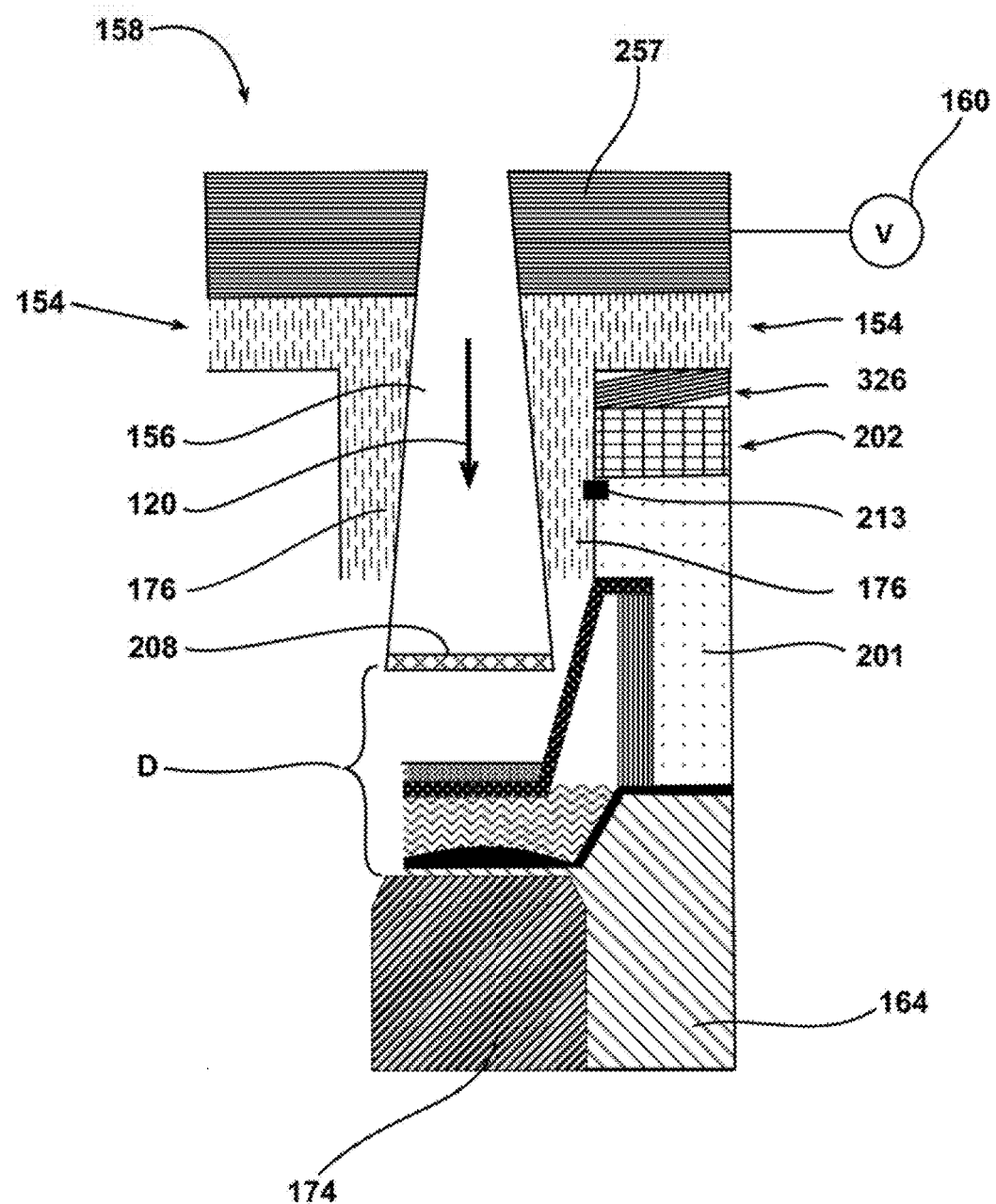
FIG. 3 is a cross-section view of another embodiment of the nanoparticle exposure chamber.

As shown in more detail in FIGS. 2-3, the distance between the wire mesh and the grounded electrode 174 may be adjusted to achieve the desired electrical field strength. In one embodiment, this distance may range from about 0.15 to 5.2 mm, depending on the height adjustment of the conical inlet tube 156 with respect to the grounded electrode 174. In other embodiment, the distance may extend up to about 10 mm. The high voltage 160 may be constant, or it may be in the shape of a square pulse to control nanoparticle deposition and to achieve realistic dosing. The strength of the high voltage 160 may range from zero to nine kilovolts to generate an electric field from zero to fifteen kilovolts/centimeter (above which breakdown may occur, depending mostly on the humidity of the air). An oscilloscope 119 may be used to monitor the amplitude and frequency of the high voltage 160. Nanoparticle deposition increases with increasing field strength (variable) and charge (fixed by the sealed ionizing source 106). Larger nanoparticles require higher field strength for deposition.

The optimal field strength for a particular embodiment or setup may be determined by balancing the particle electrical drift velocity $\vartheta_E$ and flow velocity $\vartheta_f$ using Equation (Eq.) (1), in which Cc is the Cunningham correction factor:

$$\frac{\vartheta_E}{C_c \vartheta_f} = 1.0 \quad (1)$$

The optimal electrical field strength $E_{opt}$ may then be calculated using Eq. (2) in which μ is the air viscosity, $d_p$ is the particle diameter, q is the electron charge, <N> is the weighted average of the particle charge number, Q is the inlet flow rate, and XSA is the inlet discharge cross-sectional area:

$$E_{opt} = \frac{3\pi \mu d_p}{q\langle N \rangle} \frac{Q}{XSA} \quad (2)$$

The bipolar charge distribution is calculated using the model developed by Fuchs. The $E_{opt}$ for particles of varying sizes is shown in Table 1, in which is $\vartheta_f$ 5 mL/min per well.

TABLE 1

$E_{opt}$ for Particles 0-100 nm in Size

| $d_p$ (nm) | <N>, neg $E_{opt}\left(\frac{kV}{cm}\right)$ | <N>, pos $E_{opt}\left(\frac{kV}{cm}\right)$ |
| --- | --- | --- |
| 0 | 0.00 | 0.00 |
| 10 | −0.51 | 0.51 |
| 20 | −1.03 | 1.03 |
| 30 | −1.53 | 1.53 |
| 40 | −2.00 | 2.02 |
| 50 | −2.45 | 2.48 |
| 60 | −2.88 | 2.93 |
| 70 | −3.28 | 3.36 |
| 80 | −3.67 | 3.77 |
| 90 | −4.04 | 4.18 |
| 100 | −4.41 | 4.57 |

After circulating throughout the nanoparticle exposure chamber 158, the charged nanoparticle flow 120 then enters one or more discharge ports 176 located at the top of the nanoparticle exposure chamber 158 and enters a series of internal discharge passageways 171 before exiting the nanoparticle exposure chamber assembly 150 via an aerosol outlet 170. The aerosol outlet 170 is coupled to a HEPA filter 112 and a pump 114. The pump 114 may be coupled to the control system 110 and a pump calibrator 116. An example of a suitable pump 114 includes a GilAir® Plus pump (Sensidyne®) with adjustable flow and pressure ranges, and an example of a suitable calibrator includes the Gilian® Gilibrator®-2 Primary Air Flow Calibrator (Sensidyne®). The pump 114 helps to draw the charged nanoparticle flow 120 into the nanoparticle exposure chamber assembly 150 and may further be used to control the flow rate of the charged nanoparticle flow 120 and the charged nanoparticle discharge flow 172.

The nanoparticle exposure chamber assembly 150 further comprises an integrated heating and humidifying mechanism 161 to allow for in situ maintenance of cell and tissue cultures. The integrated heating and humidifying mechanism 161 may comprise any suitable device or combination of devices known in the art so long as it is capable of being entirely incorporated into the nanoparticle exposure chamber assembly 150 (with the exception of a power supply).

The integrated heating and humidifying mechanism 161 is integrated into the nanoparticle exposure chamber assembly 150 such that sterility may be maintained during operation of the nanoparticle exposure chamber assembly 150. In the embodiment depicted in FIG. 1A, the integrated heating and humidifying mechanism 161 comprises a heater-stirrer plate 162, a water bath 164, and a magnetic stir bar 166. The integrated heating and humidifying mechanism 161 maintains even heating throughout the nanoparticle exposure chamber assembly 150 and is also in direct contact with the bottom of the nanoparticle exposure chambers 158 to evenly heat the cell culture media contained within the media well (see FIGS. 2-3 for a more detailed description). The water bath 164 may further comprise a thermistor (not labeled) to monitor the temperature of the water bath 164 (feedback control to the heater/stirrer). The grounded electrode 174 may further comprise a waterproof plastic seal.

The water bath 164 may further serve as a source of humidity for the nanoparticle exposure chamber assembly 150. Humidity 169 from the water bath 164 may be carried, for example, to the internal inlet passageways 154 via one or more humidity channels 168, where the humidity 169 then enters the nanoparticle exposure chambers 158 along with the charged nanoparticle flow 120. The humidity channels 168 may further comprise a dense wicking material that helps to pull water molecules up from the water bath 164 into the internal inlet passageways 154 and prevents the charged nanoparticle flow 120 from entering the water bath 164. In addition, in some embodiments, the humidity channels 168 may extend below the water level in the water bath 164, which is at higher pressure than the internal inlet passageways 154 and further prevents any of the charged nanoparticle flow 120 from entering the water bath 164. The temperature and/or humidity may be monitored using integrated humidity and/or temperature sensors (not labeled) mounted on or near the aerosol discharge components of the nanoparticle exposure chambers 158 (see FIG. 2 for additional detail). For example, a Model SHT75 temperature and humidity sensor may be used (Sensirion). Temperature and/or humidity data may be simultaneously measured, collected, and converted from analog to digital using a converter 118 and stored using a data acquisition/logger (not separately labeled) such as a Model EK-H4 Evaluation Kit (Sensirion). The converter 118 and data acquisition/logger may be further coupled to the control system 110.

The nanoparticle exposure chamber assembly 150 may further comprise a leveling mechanism 190, which may be located on an outer surface to allow the user to easily level the nanoparticle exposure chamber assembly 150 to ensure even distribution of water in the water bath 164 and cell culture media. The leveling mechanism 190 may comprise, for example, a bubble level.

Figure 1B:
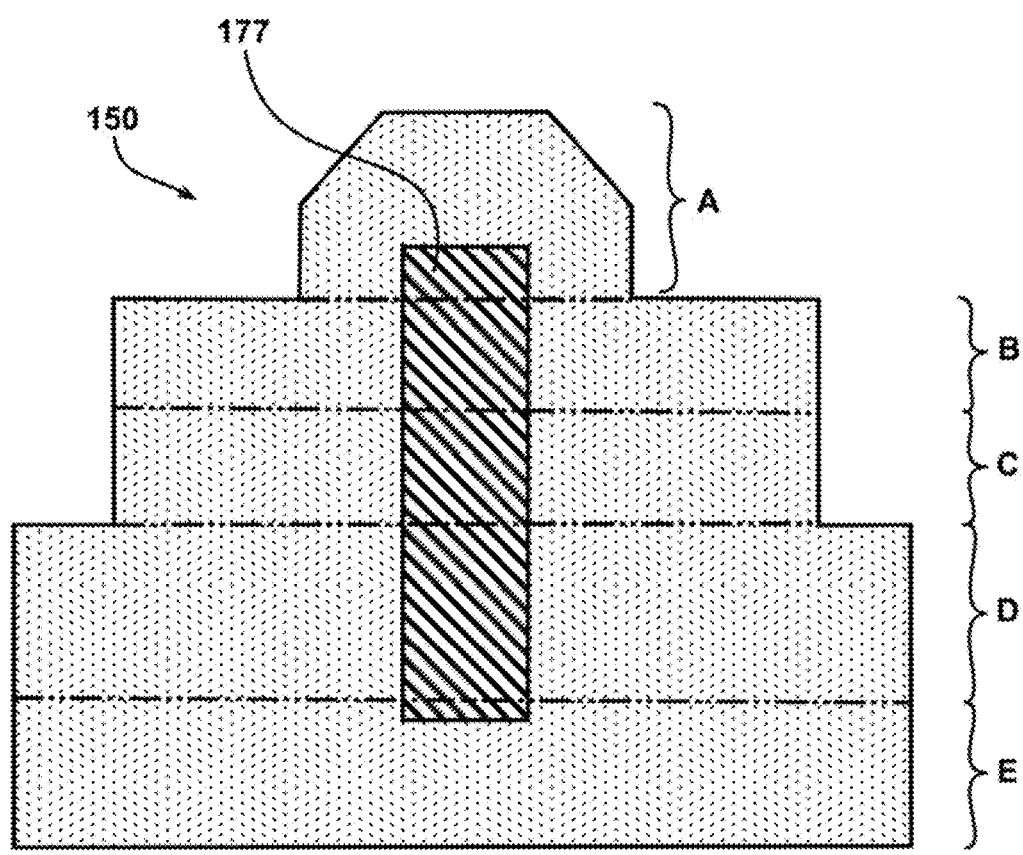
FIG. 1B is a cross-sectional view of another embodiment of the nanoparticle exposure chamber assembly comprising a plurality of stacked, modular plates.

As shown in FIG. 1B, some embodiments of the nanoparticle exposure chamber assembly 150 may comprise a plurality of modular plates A-E that may be "stacked" similar to a layer cake. The internal components of the nanoparticle exposure chamber assembly 150 are omitted in FIG. 1B for clarity. The modular plates A-E are connected along a central column 177, which serves as the central axis of the nanoparticle exposure chamber assembly 150 and may contain the aerosol inlet and outlet and internal passageways, as well as the humidity channels. In the embodiment depicted in FIG. 1B, five modular plates A-E are shown, but the number and configuration may be adjusted as needed to meet the specific requirements of each experimental setup. For example, referring to FIGS. 1A-1B, the nanoparticle exposure chamber assembly 150 may comprise a separate plate for (1) a chamber cap comprising the aerosol inlet 152 and the aerosol outlet 170, plate A; (2) an inlet plate comprising the components for applying the high voltage 160, plate B; (3) a discharge plate comprising humidity and/or temperature sensors, plate C; (4) a cell chamber plate comprising the nanoparticle exposure chamber(s) 158, plate D; and (5) a bottom plate comprising the grounded electrode 174 and other electrical components such as the heating and humidifying mechanism 161 and the thermistor, plate E.

In one embodiment, each modular plate A-E may be independently rotated about a central axis of the nanoparticle exposure chamber assembly 150 such that each modular plate A-E may be detached. For example, a central portion of modular plate A, D, and E may each comprise a plurality of threads (not labeled) that interlock with a corresponding plurality of threads on the central column 177 that is located substantially along a central axis of the nanoparticle exposure chamber assembly 150. The junctions between the modular plates A-E may comprise one or more O-rings (not labeled) or other types of sealing mechanisms that are press-sealed together when the threaded portions of modular plates A, D, and E are coupled to the central column 177 to assemble the nanoparticle exposure chamber assembly 150. This ability to independently detach each modular plate A-E allows the user to easily access various components within the nanoparticle exposure chamber assembly 150 for a variety of reasons, including adjusting experimental setups, cleaning the nanoparticle exposure chamber assembly 150, etc. The modular plates A-E also allow each component of the nanoparticle exposure chamber assembly 150 to be independently adjusted to ensure that the nanoparticle exposure chamber assembly 150 is level.

FIG. 2 is a cross-sectional view of one exemplary embodiment of a nanoparticle exposure chamber 158. Portions of the nanoparticle exposure chamber assembly 150 have been omitted or are not labeled to allow a more detailed view of the nanoparticle exposure chamber 158. The nanoparticle exposure chamber 158 comprises a cell chamber plate 201 that seals against a discharge plate 202 above and the bottom plate comprising the water bath 164 below. Above the discharge plate 202 is the inlet plate 257 to which the high voltage 160 is applied. The junction of the cell chamber plate 201 and the discharge plate 202 further comprises one or more seals 213.

The charged nanoparticle flow 120 comprising charged nanoparticles 206 enters the nanoparticle exposure chamber 158 via the conical inlet tube 156. Positioned directly beneath the conical inlet tube 156 is a target onto which the charged nanoparticles 206 are deposited. In the embodiment shown in FIG. 2, the target comprises a cell layer 212 comprising, for example, live cells or tissue culture. In some embodiments, the cell layer 212 may comprise human, animal, insect, or plant cells. In other embodiments, the cell layer 212 may comprise human lung cells or tissue culture. The cell layer 212 is contained in a cell culture insert (not separately labeled) that is held in a cell culture well 211 configured to accept the cell culture insert. The cell culture insert may be an insert suitable for growing cell and tissue culture and may comprise a porous membrane insert such as a Transwell™ cell culture insert (Corning®). The cell culture well 211 may be configured to accept a variety of sizes of cell culture inserts, and in one embodiment, the cell culture well 211 is configured to accommodate 6 and/or 12 mm cell culture inserts.

The nanoparticle exposure chamber 158 further comprises a media well 214 that holds cell culture media 216. The media well 214 is located beneath the cell culture well 211 and the cell culture insert such that the cell layer 212 in the cell culture insert is suspended in the cell culture media 216, creating an air-liquid interface. The cell culture well 211 is also configured to seal the cell culture insert within the cell chamber plate 201 such that the charged nanoparticle flow 120 does not reach the cell culture media 216. Thus, the cell layer 212 is exposed to the charged nanoparticle flow 120 on the apical (upper) surface and fed by the cell culture media 216 on the basal (lower) side. In some embodiments, each media well 214 is isolated and supplies only one nanoparticle exposure chamber 158 to protect against cross-contamination and to allow study of the cell culture media 216 from individual nanoparticle exposure chambers 158. In other embodiments, the nanoparticle exposure chambers 158 may share a common media source.

In the embodiment depicted in FIG. 2, the nanoparticle exposure chamber 158 further comprises a sleeve 218 and a channel 210 through a thickness of the cell chamber plate 201 that is open to an exterior of the nanoparticle exposure chamber assembly. The sleeve 218 forms a portion of the outer wall of the nanoparticle exposure chamber 158 and surrounds a portion of the cell culture well 211 and the cell culture insert. In some embodiments, the sleeve 218 is resealable and may comprises a silicone material providing a self-healing characteristic with an applied longitudinal compression that may, for example, reform cross-linking and reseal after being broken by a mechanical force. The sleeve 218 allows the cell culture media 216 to be replenished, for example, by passing the needle of a syringe 220 into the channel 210 and puncturing the sleeve 218 with the needle to deposit additional cell culture media 216 into the media well 214. The sleeve 218 further provides the capability for hypodermic coring to facilitate insertion of a standard introducer sheath (not labeled). The introducer sheath provides access to the media well 214 for sterile transfer of cell culture media 216 in an operational environment, potentially making the nanoparticle exposure chamber assembly 150 field deployable. An example of a suitable introducer sheath may include the CLI-100-04 introducer set (Galt Medical Corp.). The sleeve 218 may be compressed longitudinally to provide sealing to the introducer sheath, media well 214, and cell culture insert.

Because of their small size, the charged nanoparticles 206 exhibit negligible gravimetric deposition, so a force must be applied to deposit the charged nanoparticles 206 onto a target such as the cell layer 212. In the embodiment depicted in FIG. 2, electrostatic deposition is used to deposit the charged nanoparticles 206 onto the cell layer 212 by applying an electric field across the cell layer 212. A grounded electrode 174 is positioned below the nanoparticle exposure chamber 158 beneath the cell layer 112. In the embodiments shown in FIGS. 1A and 2, the grounded electrode 174 is grounded directly. In other embodiments (not shown), the media well 214 may be grounded and may serve the same function as the grounded electrode 174. The conical inlet tube 156 terminates in a slightly flared portion that includes a wire mesh 208 across the diameter of a portion of the conical inlet tube 156 near the endpoint of the conical inlet tube 156. An internal diameter of the endpoint of the conical inlet tube 156 corresponds with a diameter of the portion of the cell culture insert containing the cell layer 212 to ensure an even deposition of the charged nanoparticles 206 across the entirety of the cell layer 212. A high voltage 160 is applied to an inlet plate 257 comprising the conical inlet tube 156, with the wire mesh 208 and the grounded electrode 174 ensuring an even electric field across the cell layer 212. The electric field causes the charged nanoparticles 206 to move toward the grounded electrode 174 beneath the cell layer 212, thereby depositing at least a portion of the charged nanoparticles 206 onto the cell layer 212.

After the charged nanoparticles 206 circulate within the nanoparticle exposure chamber 158, a charged nanoparticle discharge flow 172 exits the nanoparticle exposure chamber 158 via the discharge port 176 located at the top of the nanoparticle exposure chamber 158. In the embodiment shown in FIG. 2, the discharge port 176 is an annular space formed by an integral feature in the discharge plate 202 concentrically about an outside diameter of the conical inlet tube 156 in order to provide an even flow of charged nanoparticles 206 to the nanoparticle exposure chamber 158 and to ensure an even discharge pressure for each nanoparticle exposure chamber 158. The discharge port 176 is coupled to and in fluid communication with one or more internal discharge passageways 154, and the charged nanoparticle discharge flow 172 exit the exposure chamber assembly via an aerosol outlet (not shown; see FIG. 1A). The nanoparticle exposure chamber 158 may further comprise one or more sensors 217 that may be integrated at one or more locations along the discharge port 176 and/or the internal discharge pathways. The sensors 217 may be used to monitor the temperature and/or humidity of the nanoparticle exposure chamber 158.

FIG. 3 is a cross-sectional view of another exemplary embodiment of a nanoparticle exposure chamber 158. Some components and labeling of the nanoparticle exposure chamber 158 are omitted in order to illustrate other aspects of the invention in detail. High voltage 160 is applied to the inlet plate 257 comprising the conical inlet tube 156, with the electric field strength being governed by a distance D between the grounded electrode 174 and the wire mesh 208 of the conical inlet tube 156. This distance D may be controlled and adjusted using an integrated adjustment mechanism. In the embodiment depicted in FIG. 3, the integrated adjustment mechanism comprises an adjustable threaded ring 326. The adjustable threaded ring 326 may be in addition to and independent of the central threaded portion of modular plate A, D, and E discussed with respect to FIG. 1A. The seals 213 between the discharge plate 202 and the cell chamber plate 201 maintain the integrity of the nanoparticle exposure assembly. Also as shown in the embodiment in FIG. 3, the discharge port 176 is an annular space formed by an integral feature in the discharge plate 202 concentrically about an outside diameter of the conical inlet tube 156. The discharge port 176 is coupled to and in fluid communication with one or more internal discharge passageways 154.

Referring to FIGS. 2-3, it can be seen in FIG. 2 that the conical inlet tube 156 is retracted away from the cell layer 212 such that the wire mesh 208 is almost flush with the aerosol discharge port 176, while the conical inlet tube 156 in FIG. 3 extends much further into the nanoparticle exposure chamber 158 such that D is reduced as compared to FIG. 2. In one embodiment, D comprises a range of about 0.15 mm to 5.2 mm. In other embodiment, the distance may extend up to about 10 mm. In one embodiment, the adjustable threaded ring 326 is about 12 mm thick with a 1.5 mm thread pitch. The number of threads engaged between the adjustable threaded ring 326 and the cell chamber plate 201 may be used to gauge and control D. Dosimetry of the charged nanoparticles 206 is a function of particle size and charge and the electric field (strength, shape, amplitude, frequency, etc.). The ability to adjust both the distance D between the grounded electrode 174 and the wire mesh 208 of the conical inlet tube 156 and the high voltage 160 being applied to the inlet plate 257 allows the user to precisely control the amount and rate of deposition of the charged nanoparticle 206 onto the cell layer 212 to achieve a lower dosage that better replicates in vivo exposure to NMs. By using an integrated adjustment mechanism such as the adjustable threaded ring 326, D will be the same for all nanoparticle exposure chambers 158, further allowing precise control over the nanoparticle dosage received in each nanoparticle exposure chamber 158.

Figure 4:
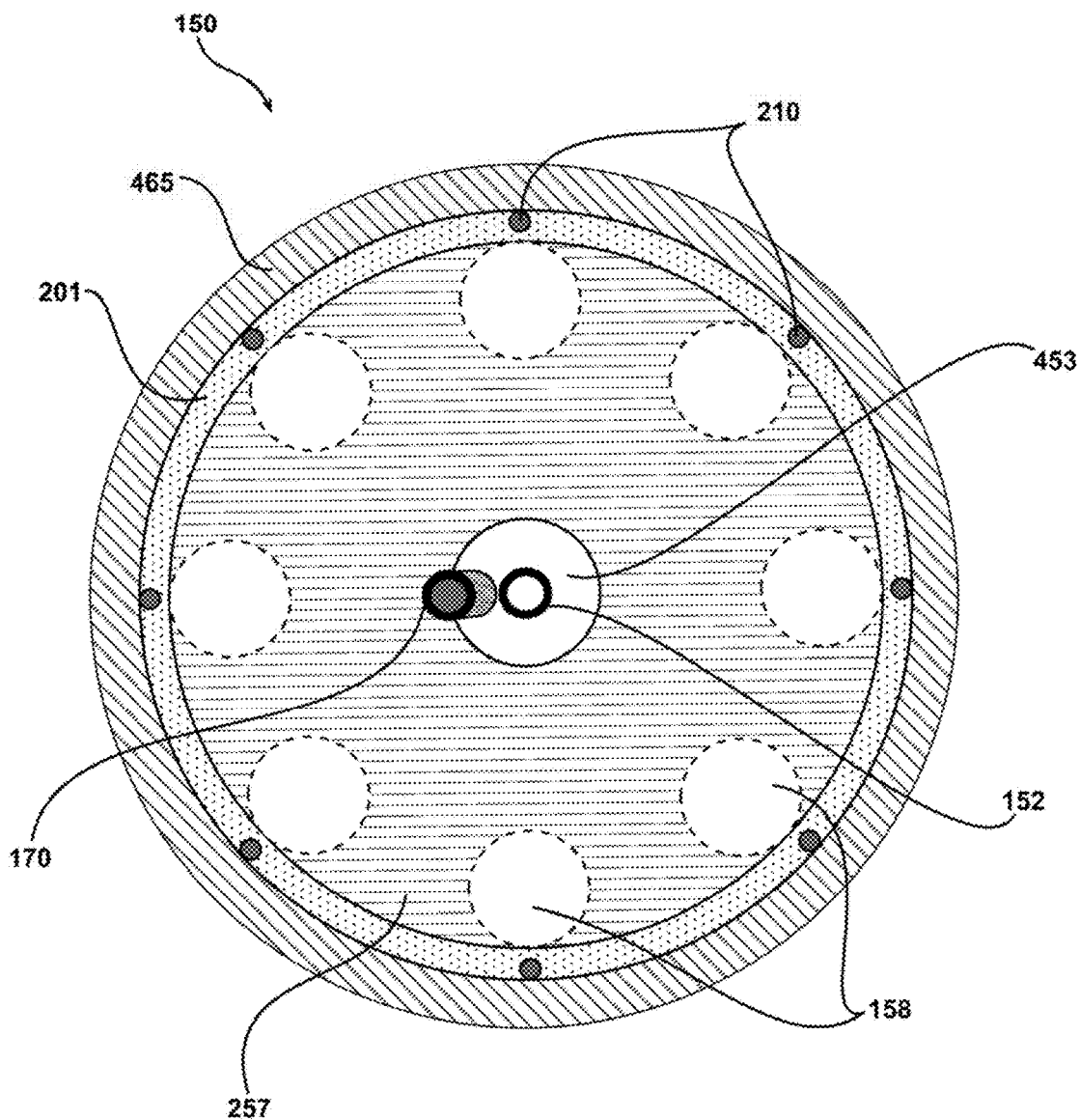
FIG. 4 is a top view of one embodiment of the nanoparticle exposure chamber assembly comprising eight, radially-arranged nanoparticle exposure chambers.

FIG. 4 is a top view of one embodiment of the nanoparticle exposure chamber assembly 150 comprising several substantially circular, modular plates, such as those depicted in FIG. 1A. Starting with the topmost plate, the chamber cap 453 comprises the aerosol inlet 152 and aerosol outlet 170. The next plate is the inlet plate 257, which comprises the internal inlet passageways (not labeled). Below the inlet plate 257 is the discharge plate (not shown), followed by the cell chamber plate 201 comprising the nanoparticle exposure chambers 158. In the embodiment shown in FIG. 4, there are eight nanoparticle exposure chambers 158 (indicated by the dashed lines) arranged radially about the central axis of the nanoparticle exposure chamber assembly 150. The cell culture plate 201 further comprises eight channels 210 that allow access to the media wells (not labeled) at the bottom of each nanoparticle exposure chamber 158. The bottom plate 465 comprises the heating/humidifying mechanism such as the water bath and heater-stirrer plate (not shown).

FIG. 5 is a cross-sectional view of a further exemplary embodiment of a nanoparticle exposure chamber 158. Some components and labeling of the nanoparticle exposure chamber 158 are omitted in order to illustrate other aspects of the invention in detail. The discharge port 176 is an annular space formed by an integral feature in the discharge plate 202 concentrically about an outside diameter of the conical inlet tube 156, with the discharge port 176 being coupled to and in fluid communication with one or more internal discharge passageways 154. In the embodiment depicted in FIG. 5, the walls of the discharge port 176 angle smoothly away from the sides of the cell culture well 211. This design promotes a uniform and non-turbulent exit of the charged nanoparticle discharge flow 172 from either side of the nanoparticle exposure chamber 158. In the embodiment depicted in FIG. 5, the discharge plate 202 comprises an integrated adjustment mechanism in the form of an adjustable threaded ring 326 that allows the conical inlet tube 156 to be easily moved up and down.

Referring to FIGS. 1-5, in addition to the seals 213 at the junction of the cell chamber plate 201 and the discharge plate 202, the nanoparticle exposure chamber assembly 150 may further comprise one or more seals throughout the apparatus (not separately labeled). These additional seals may comprise O-rings or other suitable sealing mechanisms. A person of ordinary skill in the art will appreciate that seals are required in a variety of locations to ensure that the interior of the nanoparticle exposure chamber assembly 150 remains sterile and to prevent any of the charged nanoparticles 206 from escaping. In addition, the nanoparticle exposure system 100 and nanoparticle exposure chamber assembly 150 may comprise additional wiring, connectors, sensors, and other components necessary to fully seal the nanoparticle exposure chamber assembly 150 and to make the nanoparticle exposure system 100 fully functional and operable.

Still referring to FIGS. 1-5, the components of the nanoparticle exposure chamber assembly 150 may be fabricated from any suitable material(s) including stainless steel, aluminum, and composites and plastics such as polycarbonate, medical grade polyether ether ketone (PEEK), and medical grade silicone. Stainless steel is highly conductive and stable, and the components comprising stainless steel may include the bottom plate 465 comprising the heating/humidifying mechanism and all components requiring electrical conductivity such as the inlet plate 257 and all component surfaces in contact with the charged nanoparticle flow 120 prior to cell contact. The stainless steel may comprise, for example, type 316 stainless steel. Aluminum may be used for other metal components due to its light weight and machinability. PEEK may be used for the portions of the nanoparticle exposure chamber assembly 150 that are in contact with the cell culture components. PEEK is particularly desirable due to its stability when exposed to sterilization by heat/steam (autoclave), UV light, and alcohol. Polycarbonate may be used for components requiring electrical and thermal insulating properties such as the cell chamber plate 201 and other portions of the nanoparticle exposure chamber surrounding the conical inlet tube 156 and the discharge port 176. Penetrable, medical grade silicone may be employed to form the sleeves 218, which form a portion of the nanoparticle exposure chamber 158.

While the primary use of the nanoparticle exposure system 100 may be deposition of NMs onto cell cultures for in vitro toxicity studies, the nanoparticle exposure system 100 may also be used in a higher flow-rate mode to deposit airborne NMs onto multiple substrates or multiple types of substrates such as electron microscope grids, substrates for use with atomic force microscopy, and or glass slides in order to characterize the NMs. This mode of use may be particularly valuable for field studies, as common electrostatic deposition devices for this purpose only allow for collection onto one substrate at a time (e.g. Nanometer Aerosol Sampler Model 3089, TSI®).

The following examples and methods are presented as illustrative of the present invention or methods of carrying out the invention, and are not restrictive or limiting of the scope of the invention in any manner.

Example 1

Simulation of Gas Flow, Electrostatics, and Particle Deposition

Using an embodiment of the nanoparticle exposure system similar to that depicted in FIG. 5, simulations of the flow field, electrical field, and particle trajectories in a single nanoparticle exposure chamber were conducted using COMSOL Multiphysics® software (Comsol® Inc.). In the simulated chamber, the conical inlet tube discharge had a cross-sectional area of 0.1772 $cm^2$. The steady-state computational fluid dynamics module was used to establish the flow in the chamber. The normal inlet flow velocity was set so that the discharge velocity was equivalent to 0.0047 m/s, calculated based on the flow rate used for deposition experiments (5 mL/min) and cross-sectional area of the conical inlet tube discharge. The steady-state electrostatics module was used to establish the electric field in the chamber. The electric potential was applied at the conical inlet tube discharge and ground to the media well. When the wire mesh across the conical inlet tube discharge is present, substantially horizontal linear electric potential lines are generated. When the wire mesh is not present, the electric potential lines are not linear and curve upward toward the conical inlet tube (not shown).

The time-dependent particle tracing module of the COMSOL Multiphysics® software was then used to track the behavior of spherical micron-sized particles (10 μm diameter) and nano-sized particles (100 nm diameter) under these conditions (data not shown). Simulations were performed using an electric potential of 0, −3, and −5 kV/cm that was applied to the conical inlet tube discharge with a wire mesh. At 0 kV/cm, the micron-sized particles deposit in the center of the deposition layer by impaction, while the nano-sized particles flow along with the air stream and do not deposit. At −3 kV/cm, deposition occurs uniformly across the deposition layer, indicating that −3 kV/cm is at or near an optimal field strength. Focusing of the particles toward the center of the deposition layer begins to occur at −5 kV/cm, indicating that this electric potential creates a field strength that is too high. These values are consistent with $E_{opt}$ calculated in Table 1. This simulation further demonstrates that generation of an electric field is essential for uniform particle deposition.

Example 2

Deposition of Nanoparticles in an Eight-Chamber Assembly

Several experiments were conducted using silver nanoparticles to observe particle deposition in the chambers of an eight-chamber nanoparticle exposure chamber assembly with chambers similar to the embodiment depicted in FIG. 5. The humidity and temperature were monitored in each chamber using a Sensirion Model SHT75 sensor that was mounted near the cell layer in the aerosol discharge path. The air temperature was maintained at 27.18±0.05° C. and relative humidity at 68.68±1.42%. Silver nanoparticles coated with polyaromatic pyrolized hydrocarbons (25 nm, Novacentrix®) were aerosolized from a powder using the Vilnius Aerosol Generator (CH Technologies, Inc.). A scanning mobility particle sizer (NanoScan, TSI®) was used to measure the number size distribution and total number concentration over time. The mass size distribution was calculated for each size bin using Eq. (1), assuming spherical particle morphology and diameter equivalent to the value for each size bin. The silver nanoparticles were grouped into size bins ranging from 11.5 to 365.2 nm.

Figure 6:
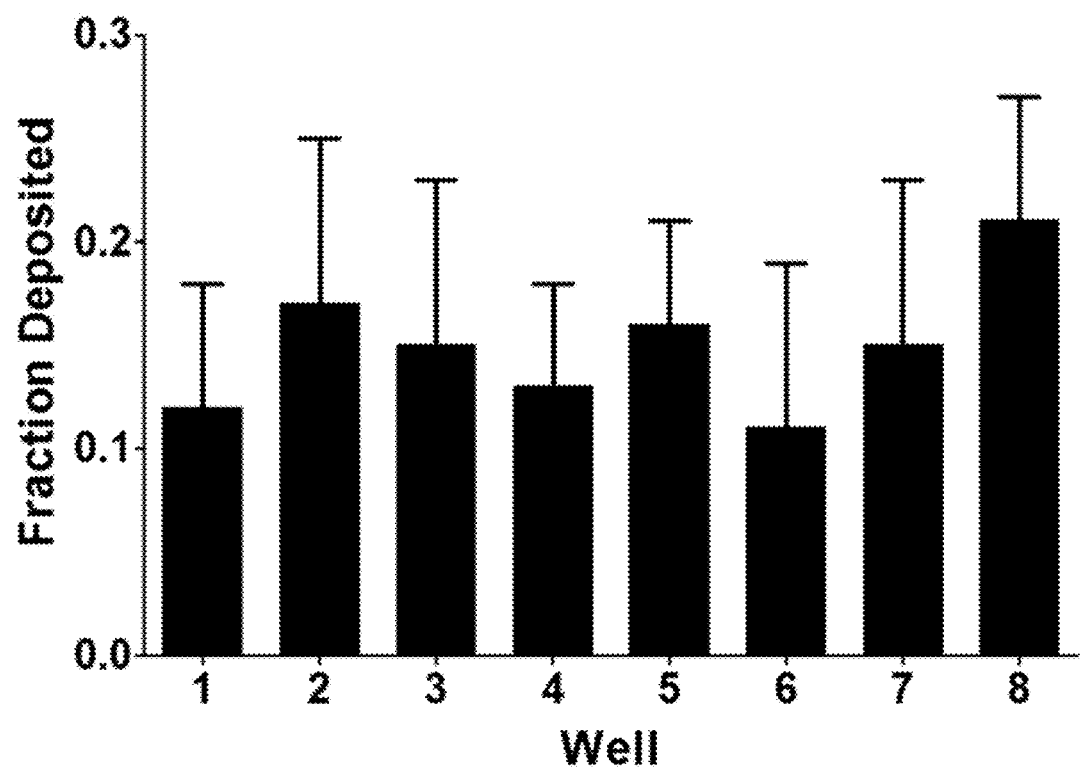
FIG. 6 is a graph illustrating the fraction of silver nanoparticles deposited per chamber in an eight-chamber assembly.

The aerosolized silver nanoparticles were then passed through the chamber assembly at a flow rate of 5 mL/min per chamber and subjected to a field strength of either 0 or 5 kV/cm. The total mass deposited in all eight wells was evaluated for three separate trials using inductively coupled plasma-mass spectrometry. As demonstrated in the simulations described in Example 1, the total mass of deposited nanoparticles was much higher when an electric field was applied (data not shown). In addition, as shown in FIG. 6, the deposition fraction (the mass of silver deposited in each well relative to the total mass deposited for each trial) was calculated and averaged for the three trials across the eight chambers to ensure relatively even dosing of each chamber with nanoparticles.

Example 3

Deposition of Nanoparticles on Type II Pneumocytes

Human type II pneumocytes (A549, ATCC) were grown in the nanoparticle exposure chamber assembly with chambers similar to the embodiment depicted in FIG. 5. The cells were grown at 37° C. and 100% humidity. The cell culture media was replaced using a syringe inserted into the silicone sleeves on the outside of each chamber. No change in flow rate was observed after insertion of the syringe into the silicone sleeves. The cells were examined using the live cell alamarBlue® assay (Invitrogen®), which was completed according to the manufacturer's instructions.

Figure 7:
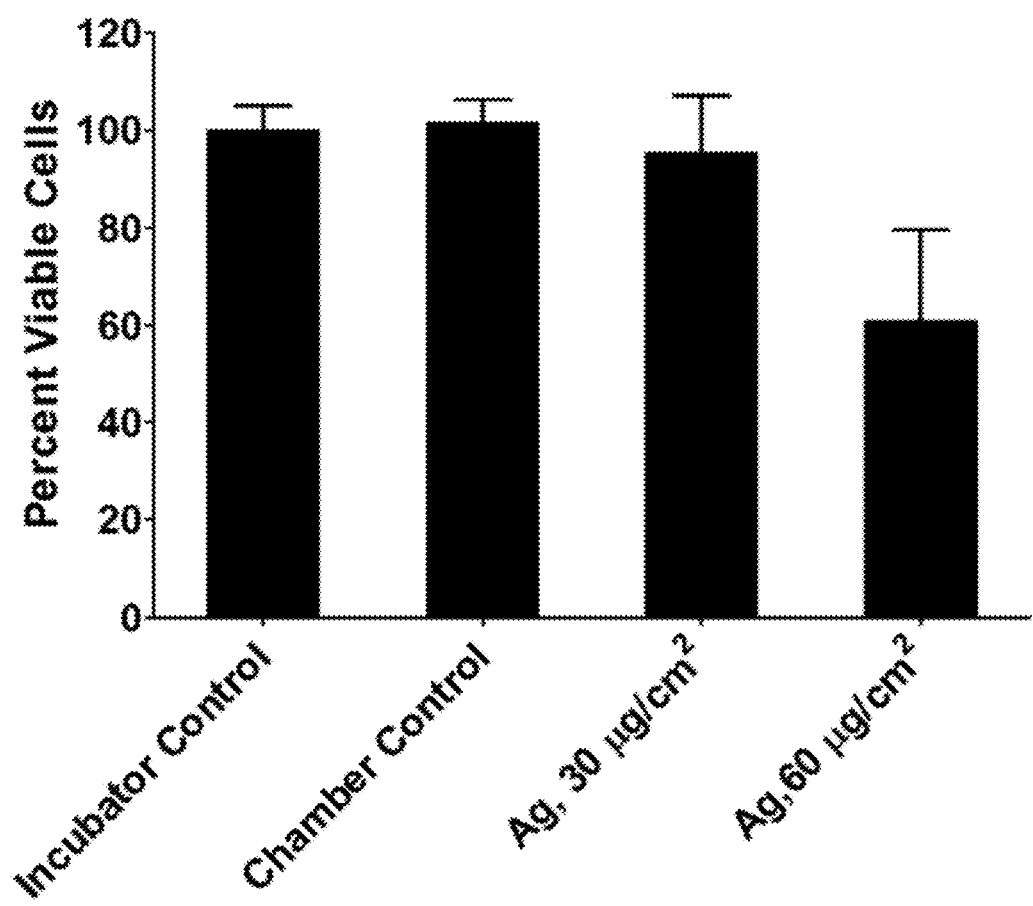
FIG. 7 is a graph illustrating the number of viable cells following exposure to varying concentrations of silver nanoparticles.

As shown in FIG. 7, there was no difference in terms of the number of viable cells between the cells grown in a standard incubator (Incubator Control) as compared to cells in the chamber that were exposed to 1 hour, 5 kV/cm field strength with 40 mL/min flow (Chamber Control). A concentration dependent decrease in cell viability was observed for exposure to silver (Ag) nanoparticles, 30 and 60 μg/cm². The cells exposed to 60 μg/cm² demonstrated a statistically significant reduction in cell viability as compared to the Chamber Control and cells exposed to 30 μg/cm² of silver. The cell morphology was examined in the Chamber Control and the cells exposed to 60 μg/cm² of silver nanoparticles by staining the actin with phalloidin-Alexa Fluor® 555 (Invitrogen®) and nuclei with DAPI (Invitrogen®) according to the manufacturer's instructions (not shown). The morphology of the cells was not significantly affected. Silver particles were detected all the way out the edges of the cell layer, indicating suitable chamber design and sufficient electric field strength to achieve deposition without focusing.

Example 4

Deposition of Nanoparticles onto a TEM Grid

Silver nanoparticles stabilized in citrate (60 nm, Ted Pella, Inc.) were aerosolized using electrospray to produce a well-dispersed nanoparticle aerosol. The silver nanoparticles were deposited onto a formvar-carbon coated copper grid placed at the deposition layer in well eight of the chamber in the presence of a field strength of −3 kV/cm. A total of 24 images were acquired at 4,000 times magnification using a transmission electron microscope (Hitachi® H-7600, Hitachi, Ltd.). Particles in each image of 565.25 square microns were counted, then averaged and divided by the surface area. The micrographs (not shown) indicated successful and uniform distribution of the silver nanoparticles on the TEM grid.

Therefore, these Examples demonstrate that the presently disclosed nanoparticle exposure chamber assembly provides a flexible and versatile setup that may be altered to accommodate a variety of cell culture inserts and may be used not only for in vitro toxicity studies but also to deposit nanoparticles on a variety of substrates for further study. The design of the nanoparticle exposure chamber assembly may be scaled up or down to create an apparatus with the desired number of chambers, and different chambers within the same apparatus may be used for different experiments. In addition, the presently disclosed apparatus provides fully integrated heating and humidity components and internal humidity and temperature monitoring so that cell cultures may remain in the apparatus throughout the entirety of the experiment, which reduces cell stress and maintains sterility, thereby allowing better replication of in vivo conditions. Furthermore, the multi-chamber design and ability to uniformly adjust the distance between the aerosol inlet and the cell membrane and/or electrode allow for administration of lower, precisely controlled, biologically relevant doses of NMs over a longer period of time, which better replicates in vivo exposure conditions.

Although specific embodiments have been described in detail in the foregoing description and illustrated in the drawings, various other embodiments, changes, and modifications to the disclosed embodiment(s) will become apparent to those skilled in the art. All such other embodiments, changes, and modifications are intended to come within the spirit and scope of the appended claims.

What is claimed is:

1. A nanoparticle exposure system comprising:
a gas supply, wherein the gas supply provides a gas flow;

an aerosol nanoparticle generator coupled to and in fluid communication with the gas supply, wherein the aerosol nanoparticle generator generates a plurality of charged nanoparticles using an electrospraying process, the charged nanoparticles mixing with the gas flow from the gas supply to form a charged nanoparticle flow;

an ionizing source coupled to and in fluid communication with the aerosol particle generator;

a nanoparticle exposure chamber assembly coupled to and in fluid communication with the ionizing source, wherein the nanoparticle exposure chamber assembly comprises at least one nanoparticle exposure chamber;

a high voltage source coupled to the nanoparticle exposure chamber assembly such that a high voltage is applied to the at least one nanoparticle exposure chamber;

an exterior pump coupled to the nanoparticle exposure chamber assembly;

a control system coupled to at least one component of the nanoparticle exposure system such that the control system regulates operation of and logs data from the nanoparticle exposure system;

an aerosol inlet, wherein the aerosol inlet is coupled to and in fluid communication with the ionizing source such that the charged nanoparticle flow enters the nanoparticle exposure chamber assembly;

at least one inlet passageway, wherein each inlet passageway is coupled to and in fluid communication with the aerosol inlet and terminates in a conical inlet tube, each conical inlet tube further comprising a wire mesh across a diameter of the conical inlet tube, wherein each conical inlet tube is coupled to and in fluid communication with one of the at least one nanoparticle exposure chambers;

a discharge port coupled to and in fluid communication with one of the at least one nanoparticle exposure chambers, wherein each discharge port is configured concentrically around an outside diameter of one conical inlet tube, the discharge port further being coupled to and in fluid communication with at least one outlet passageway, wherein each outlet passageway is coupled to and in fluid communication with an aerosol outlet, the aerosol outlet being coupled to and in fluid communication with the exterior pump; and an integrated heater and humidifier comprising a heat source and a humidity source, the integrated heater and humidifier being coupled to and in fluid communication with at least one inlet passageway, wherein at least a portion of each nanoparticle exposure chamber further comprises a resealable sleeve that surrounds a cell culture well, wherein the nanoparticle exposure chamber assembly further comprises a channel between the resealable sleeve and an exterior of the nanoparticle exposure chamber assembly, the channel angled downward through the resealable sleeve and toward cell culture media in a media well below the cell culture well, the channel and the resealable sleeve permitting the cell culture media in the media well to be replenished or replaced without compromising sterility of the nanoparticle exposure chamber assembly.

2. The nanoparticle exposure system of claim 1 wherein the ionizing source is configured to partially neutralize the charged nanoparticles such that the charged nanoparticles remain uniformly distributed as an aerosol within the charged nanoparticle flow.

3. The nanoparticle exposure system of claim 1 wherein each nanoparticle exposure chamber comprises:

a cell culture well configured to receive a cell culture insert, the cell culture insert being configured to hold a target, with the cell culture well located directly beneath the conical inlet tube;

a media well comprising cell culture media, wherein the media well is located beneath the cell culture well such that at least a portion of the target is in contact with the cell culture media to create an air-liquid interface, the media well further being located such that the integrated heater and humidifier is in contact with the media well, and a grounded electrode located beneath the media well.

4. The nanoparticle exposure system of claim 3 wherein the integrated heater and humidifier further comprises a wicking material that facilitates entry of humidity from the humidity source into the at least one inlet passageway.

5. The nanoparticle exposure system of claim 3 wherein the high voltage source is coupled to the nanoparticle exposure chamber assembly such that an electric field is applied across the target, an electric field strength being dependent on a distance between the wire mesh and the grounded electrode, wherein the nanoparticle exposure system is configured to deliver a dose of charged nanoparticles over a predetermined period of time.

6. The nanoparticle exposure system of claim 5 wherein the nanoparticle exposure chamber assembly is configured such that the distance between the wire mesh and the grounded electrode for each nanoparticle exposure chamber is adjustable by a common adjustment mechanism, wherein the distance is the same for all nanoparticle exposure chambers.

7. The nanoparticle exposure system of claim 1 comprising two or more nanoparticle exposure chambers that are arranged radially about a central axis of the nanoparticle exposure chamber assembly.

8. The nanoparticle exposure system of claim 1 wherein the exterior pump draws the charged nanoparticle flow into the nanoparticle exposure chamber assembly.

9. The nanoparticle exposure system of claim 1 wherein the nanoparticle exposure chamber assembly further comprises a plurality of modular stacking plates arranged about a central axis of the nanoparticle exposure chamber assembly, wherein the modular stacking plates are interconnected, each modular plate comprising a portion of the nanoparticle exposure chamber assembly and being configured to be independently adjusted.

10. The nanoparticle exposure system of claim 1 further comprising at least one particle characterization device.

11. The nanoparticle exposure chamber assembly of claim 3 wherein the integrated heater and humidifier is in contact with the media well such that the cell culture media is maintained at or near 37° C.

* * * * *